United States Patent
Duncan et al.

(10) Patent No.: US 9,458,322 B2
(45) Date of Patent: Oct. 4, 2016

(54) SELF-ASSEMBLED NANO-STRUCTURE PARTICLE AND METHOD FOR PREPARING

(71) Applicant: EMERALD HILTON DAVIS, LLC, Cincinnati, OH (US)

(72) Inventors: Gregory D. Duncan, Wyoming, OH (US); Kevin M. Henry, Lockland, OH (US); Joseph D. Kern, Montgomery, OH (US)

(73) Assignee: EMERALD HILTON DAVIS, LLC, Cincinnati, OH (US)

( * ) Notice: Subject to any disclaimer, the term of this patent is extended or adjusted under 35 U.S.C. 154(b) by 0 days.

(21) Appl. No.: 14/346,339

(22) PCT Filed: Sep. 21, 2012

(86) PCT No.: PCT/US2012/056597
§ 371 (c)(1),
(2) Date: Mar. 21, 2014

(87) PCT Pub. No.: WO2013/044045
PCT Pub. Date: Mar. 28, 2013

(65) Prior Publication Data
US 2014/0238271 A1    Aug. 28, 2014

Related U.S. Application Data (60) Provisional application No. 61/538,175, filed on Sep. 23, 2011.

(51) Int. Cl.
C09B 67/20 (2006.01)
A61K 47/48 (2006.01)
(Continued)

(52) U.S. Cl.
CPC ..... *C09B 67/0066* (2013.01); *A61K 47/48961* (2013.01); *B82Y 5/00* (2013.01);
(Continued)

(58) Field of Classification Search
None
See application file for complete search history.

(56) References Cited

U.S. PATENT DOCUMENTS

| | | | |
|---|---|---|---|
| 4,365,061 A | 12/1982 | Szejtli et al. | |
| 4,990,280 A * | 2/1991 | Thorengaard | C11D 3/0063 427/213.3 |

(Continued)

FOREIGN PATENT DOCUMENTS

| | | |
|---|---|---|
| CA | 2181495 A1 | 1/1997 |
| JP | 63 199781 A | 8/1988 |

(Continued)

OTHER PUBLICATIONS

Zhao, B., et al., Adhesion and detachment mechanisms of sugar surfaces from the solid (glassy) to liquid (viscous) states, PNAS, Dec. 26, 2006, vol. 3, No. 52, pp. 19624-19629.

(Continued)

*Primary Examiner* — Jeffrey Washville
(74) *Attorney, Agent, or Firm* — Hudak, Shunk & Farine Co., LPA (57) ABSTRACT

Novel, nano-structured particles are formed by introducing a selected solid of interest into a structured fluid matrix formed by a dispersion of a small molecule host vessel, such as a native or modified polysaccharide, cavitand, simple sugar, simple polyol or other similarly structured molecule known to be useful as a host vessel, in an acidic medium or other solvent, whereby the particle size of the introduced solid is reduced and or limited by incorporation into the host vessel. The simple, one-step mixing process results in stabilized colloidal dispersions of the nanoparticles useful in a wide variety of applications.

7 Claims, 3 Drawing Sheets

(51) Int. Cl.
*B82Y 5/00* (2011.01)
*C09B 67/00* (2006.01)
*C09B 67/02* (2006.01)
*C09B 67/46* (2006.01)

(52) U.S. Cl.
CPC ........ *C09B 67/009* (2013.01); *C09B 67/0022* (2013.01); *C09B 67/0023* (2013.01); *C09B 67/0067* (2013.01); *C09B 67/0097* (2013.01)

(56) References Cited

U.S. PATENT DOCUMENTS

| | | | |
|---|---|---|---|
| 6,048,736 A | | 4/2000 | Kosak |
| 6,171,381 B1 | | 1/2001 | Yoshimura et al. |
| 6,881,421 B1 | | 4/2005 | da Silveira et al. |
| 7,030,176 B2 | | 4/2006 | Nohr et al. |
| 7,307,110 B2 | | 12/2007 | Yatake |
| 7,371,456 B2 | | 5/2008 | Nohr et al. |
| 7,462,659 B2 | | 12/2008 | Rhee et al. |
| 7,741,384 B2 | | 6/2010 | Liu |
| 7,829,698 B2 | | 11/2010 | Kim et al. |
| 2002/0134280 A1 | | 9/2002 | Naruse |
| 2003/0195274 A1 | * | 10/2003 | Nakamura ............... B01J 13/04 523/160 |
| 2004/0265237 A1 | | 12/2004 | Kim et al. |
| 2005/0084535 A1 | | 4/2005 | Coleman et al. |
| 2008/0044481 A1 | * | 2/2008 | Harel ...................... A61K 9/127 424/490 |
| 2010/0173002 A1 | * | 7/2010 | Yulai ..................... A23L 1/0029 424/492 |
| 2011/0150954 A1 | | 6/2011 | Lapidot et al. |

FOREIGN PATENT DOCUMENTS

| | | |
|---|---|---|
| JP | 01 146974 A | 6/1989 |
| JP | 11 106694 A | 4/1999 |
| JP | 2000160077 A | 6/2000 |
| JP | 2001271012 A | 10/2001 |
| JP | 2005350586 A | 12/2005 |
| JP | 2006316225 A | 11/2006 |
| KR | 100258640 B1 | 6/2000 |

OTHER PUBLICATIONS

Padrino, J.C., et al., Stress-induced cavitation for the streaming motion of a viscous liquid past a sphere, J. Fluid Mech., 2007, vol. 578, pp. 381-411.

Dellinger, T.M., et al., BiOCl Nanoparticles Synthesized in Lyotropic Liquid Crystal Nanoreactors, Scripta mater, 2001, vol. 44, Nos. 8/9, pp. 1893-1897.

Ruths, M., et al., Rate-Dependent Adhesion between Polymer and Surfactant Monolayers on Elastic Substrates, Langmuir 1998, vol. 14, No. 7, pp. 1804-1814.

* cited by examiner

Helical structure of Amylose from starch. Starch is composed of amylose and amylopectin, and maltodextrins are the product of partial hydrolysis of starch. Regions within the amylose helix are known to be relatively hydrophobic and can host inclusions.

FIG. 1

Below is the chemical structure of β-cyclodextrin together with schematics representing structures and dimensions for α, β, and γ-cyclodextrins. Cyclodextrins are members of a class of molecules known as cavitands that are very effective at hosting guest molecules within their central cavity.

Below is a computer generated space filling model of β-cyclodextrin.

FIG. 3

SELF-ASSEMBLED NANO-STRUCTURE PARTICLE AND METHOD FOR PREPARING

FIELD OF THE INVENTION

This invention is directed to novel, stable colloidal dispersions of self-assembled nano-structured particles formed within a gel comprising native or modified polysaccharides, cavitands and other similar molecules, and methods for preparing them. This invention is also directed to useful applications for the inventive colloidal dispersions.

BACKGROUND OF THE INVENTION

Nanostructures or nanoparticles are plentiful in nature and form the basic building blocks for chemical and biological compositions. Nanoparticles may also be created by artificial means, either chemical or mechanical, or both, to take advantage of property improvements associated with their use. Use of nanoparticles allows greater accessibility and availability of many components for certain applications and may reduce the amount of a component necessary to achieve a given result, thus reducing costs attendant with the use of the component. Small particle size is itself a necessary property for colloidal stability and for high performance of particle dispersions in some applications, including jetting.

Small particles, and in particular, nanoparticles, may be prepared either by reducing the size of larger particles or by constraining growth of particles as they are formed, or by a combination of techniques. For example, the size of larger particles may be reduced by any number of mechanical or physical techniques known to those skilled in the art. These techniques include, without limitation, the application of energy through milling, ultrasound or high sheer mixing, such as, but not limited to, a media mill, ball mill, an attritor, a flow jet mixer, an impeller mill, a colloidal mill, or a sand mill. Alternatively, smaller particles may be formed during synthesis by constraining their growth, for example, by formation in a micro-channel reactor. Finally, particle size may be reduced by dissolving larger particles and constraining growth during recrystallization. This may be accomplished, for example, by precipitating the particles from solution in the presence of surfactants, among other methods known in the art.

More recently, it has been reported that nanostructured particles of inorganic minerals have been formed in lyotropic liquid crystals having hydrophilic and hydrophobic domains within the crystal. This method is not used commercially.

The prior art techniques for creating small particles are not without shortcomings. Typically, the most effective commercial techniques to obtain small particles, including nanoparticles, require reduction of the size of larger particles, accomplished by the application of mechanical or physical energy or constraining particle size growth, as discussed above. Both of these approaches require highly specialized equipment and are time consuming, and both the equipment and processes are expensive.

In addition, smaller particle sizes are generally associated with larger surface areas, and nanoparticles are no exception. Due to their larger surface areas, among other things, nanoparticles require stabilization to prevent agglomeration and maintain their dispersibility in suitable media, making them more accessible or available for their ultimate use. Hence, following reduction of particle size, it is typically necessary to stabilize the nanoparticle dispersion through a separate step.

Colloidal dispersions of small particles, including nanoparticles, may be stabilized by several different techniques, including without limitation i) the addition of polymeric or small molecule surfactants that associate non-covalently with the surface of the particle, ii) through covalent attachment of "stabilizing" small molecules, or iii) polymers to the surface of the small particle, or by encapsulation of the small particle with components that will contribute to the stabilization. Encapsulation may be accomplished, for example, by cross-linking polymeric surfactants or polymerizing monomers, which are then adsorbed to the surface of the particle.

Some stabilization examples from the prior art include U.S. Pat. No. 7,741,384, which is directed to a method of homogenizing a dispersion by coating pigment particles with a polymerized monomer. Similarly, U.S. Pat. No. 7,307,110 describes methods for improving dispersibility of a water-based pigment by treating the surface of the pigment particle with a water-dispersibility-imparting group or encapsulating the pigment particle with a water-dispersible polymer. U.S. Pat. No. 6,432,194 describes methods of attaching functional groups to pigment particles to improve various properties rather than relying on adsorption. U.S. Pat. No. 6,171,381 is directed to an aqueous ink composition wherein cyclodextrin is used as a coating agent; dextrins are also used as dye binders in KR 100258640.

Prior art stabilization techniques involving the addition of surfactants, covalent attachment of "stabilizing" small molecules or polymers to the surface of the particle, or encapsulation of the particle, while useful, are not without disadvantages. Surfactants may change the properties of the dispersion in undesirable ways, such as by increasing viscosity or lowering surface tension, and they may also be expensive. Practical commercial techniques to stabilize small particles by covalent attachment of small molecules or polymers and/or by encapsulation tend to require relatively complex, multi-step chemical processes and may use undesirable or dangerous solvents or reagents. There is, therefore, a need for a process for preparing stabilized nanoparticle dispersions that allow for accessibility and availability of the nanoparticle component in the selected application, without compromising the properties of the dispersion and that are simple and cost effective to produce.

Novel self-assembled nanoparticles and unique processes for preparing them have been discovered, which avoid the shortcomings of the prior art discussed above. The novel self-assembled nanoparticles of the invention are clathrates formed by the addition of a selected guest solid to a structured fluid or matrix, i.e., a semi-solid or viscoelastic gel comprising a host vessel or molecule dispersed in an acid or other solvent medium. The host vessel may comprise a number of compounds known to one skilled in the art to be useful as host molecules in supra-molecular chemistry. These include: native or modified polysaccharides; cavitands, such as cyclodextrin, cucurbituril and calixerenes; simple sugars, such as dextrose, fructose or glucose; simple (linear, branched, or cyclic) polyols, such as ethylene glycol, propylene glycol, glycerin, sorbitol and xylitol; crown ethers, aza crowns, cryptands, cyclophanes, oligo- and poly-peptides, proteins, oligo- and poly-nucleotides, or other similarly structured molecules. The selected guest solid is entrapped or otherwise included within the host vessel to form a clathrate cage or shell having the selected solid (guest) encompassed within. The particle size of the selected solid is thus reduced or growth is limited by the structural constraints of the host molecule.

Clathrate or host/guest formations are known in the art, although none of the prior art describes the specific clathrates of the present invention, or processes, for reducing particle size of a selected solid to nanoparticle dimensions through the use of a clathrate and/or stabilizing a colloidal dispersion of nanoparticles, which do not require additional particle size reduction or stabilizing steps. For example, U.S. Patent Publ. No. 2004/265237 discloses a small molecule clathrate useful for improving the solubility and release of platinum based anticancer drugs, but the disclosed clathrate is not a nanoparticle-based clathrate. Similarly, U.S. Pat. No. 6,881,421 discloses a nano-polyalkylcyanoacrylate plus an inclusion compound useful for complexing an "active" in its hydrophobic cavity, useful as a drug carrier. U.S. Pat. No. 7,462,659 discloses uniform nanoparticles useful as pore-forming templates on wafers of electronic material, wherein cyclodextrin is combined with silica to form a low dielectric film. U.S. Pat. No. 7,829,698 describes nanoparticles comprising cucurbituril derivatives and pharmaceutical compositions in THF organic solvent for use as a drug delivery system.

With respect to inks and jetting applications in particular, none of the prior art discloses the novel nanoparticle-based aqueous colloidal dispersions of the present invention. JP 2001271012 describes a nanoparticle-based ink formulation prepared by first mechanically reducing the particle size of the pigment and combining the pigment with a number of components including amides, polyhydric alcohols, urea, glycerin, glycols, ethers, buffers, and water. Cyclodextrin or calixarene are added to aid in dispersibility and stability of the formulation in the same manner as surfactants.

By contrast, the present invention does not require or utilize reduction of the particle size of the selected solids to nanoparticle dimensions prior to addition to the gel. Rather, reduction of selected solids to nanoparticles is accomplished in a one-step mixing process involving the addition of the selected solid to a gel comprising a host vessel or molecule dispersed in an acid medium or other solvent. Particle size reduction is accomplished by dissolving and reforming the solid in the host vessel, or by synthesizing the solid directly in the host vessel and annealing the interaction. Mechanical particle size reduction might be used prior to combining the selected solid with the gel, but only for particularly large particles or agglomerates to facilitate further reduction to nanoparticles using the inventive process. The invention yields stable colloidal dispersions without the addition of other steps or components.

CA2181495 discloses a water-based printing ink comprising an epoxy, an organic or inorganic pigment, a drier, cyclodextrin and water. Cyclodextrin forms an "inclusion compound" with the drier to protect it and to reduce the amount needed in the ink. Unlike the present invention, the cyclodextrin is not used as a host for the pigment, nor is it stated to reduce the particle size of the selected pigment.

U.S. Pat. Nos. 7,371,456 and 7,030,176 disclose new recording inks with improved properties comprising nanoparticles with colloidal inner cores used as a template to bind a series of layers of colors and a complex process for preparing them. The inks include optional "includant" compounds that may inhibit aggregation of the colors or add to the stability of the inks and cyclodextrin is listed as one such compound. Stability is primarily accomplished by charges on pre-formed polymers. Unlike the present invention, the inks require alternating layers of polymers and/or charged polymers to wrap or attach to colorants. The inks are formed in an oil/water system by high sheer emulsification, using organic solvents. In addition, preparation of the inks starts with a charged nano-particle core of either a charged polymer or a charged silica gel particle. Nothing in either of these patents teach the use of includant compounds to reduce particle size or stabilize the formulation.

The present invention is also directed to novel processes to achieve the novel self-assembled nanoparticles, colloidal dispersions thereof, and colloidal stabilization in a single step mixing process that is safe and environmentally friendly. The inventive processes involve the use of simple techniques to prepare nano-structured particles and stable colloids of these particles that may be easily practiced in, and are viable for, commercial manufacturing. The novel processes are also less costly, because they do not require specialized or additional equipment or steps, specialized handling or additional components.

Nano-structured particles prepared by the inventive processes have many valuable uses, among them are as stable colloidal dispersions useful for application by jetting technology. Stable, colloidal dispersions of organic color pigments have been prepared using this technology. These dispersions have been used to prepare inks with excellent jetting properties, although the invention is not limited to this application. Other uses of the novel, stable colloidal dispersions of the present invention include, but are not limited to, other types of inks and coatings; preparation of stable colloids of electronic materials such as conductors, insulators, semiconductors, and the like, particularly those useful for devices or manufacturing as by jetting; preparation of stable dispersions of organic and ceramic materials for various other applications; preparation of stable dispersions for biotechnology, pharmaceutical, drug delivery, medical diagnostics or bioassays, or imaging applications; and nano-fabrication of devices. Other uses will be evident to one skilled in the art.

The novel, stable colloidal dispersions of the invention have comparable particle size and comparable or better stability than those produced by traditional competitive processes and have demonstrated utility in jetting applications.

It is an object of the invention to provide a simple, one step method for reducing the particle size of a large variety of solids to nanostructured particles.

It is a further object of the invention to provide stabilized colloidal dispersions of nanoparticles from a wide variety of selected solids.

It is yet another object of the invention to provide commercially viable techniques for producing stabilized colloidal dispersions of nanoparticles of a wide variety of selected solids, which are simple, safe, cost effective and environmentally friendly to perform.

SUMMARY OF THE INVENTION

The invention is directed to novel nano-structured particles and stable colloidal dispersions thereof, novel methods to reduce the particle size of a solid to nanoparticle dimensions by formation in a clathrate structure, and novel methods to prepare clathrate-based structured fluids useful for reducing particle size of a solid and producing stable colloidal dispersions of nanoparticles, without the need for conventional stabilization techniques. In contrast to conventional particle size reduction techniques, the inventive techniques allow for reduction in the particle size of the selected solid to nanoparticles and stabilization of a colloidal dispersion of the nanoparticles so formed in a single step—by annealing in a gel comprising native or modified polysaccharides, cavitands, or other similarly structured molecules known to be useful host vessels in a fluid. The viscoelastic or semi-solid gel resulting from the dispersion of the host vessel in an acid or other solvent is a "structured" fluid matrix that acts as a template for reducing the particle size of an added solid or limiting the growth of particles of compounds that are synthesized within the gel. The colloidal dispersions formed are useful in a number of applications, including but not limited to inkjet applications and other applications discussed above.

In one embodiment, the invention is a novel structured fluid matrix comprising host vessels formed from native or modified polysaccharides, cavitands, simple sugars, such as dextrose, fructose and glucose, simple (linear, branched, or cyclic) polyols, such as ethylene glycol, propylene glycol, or glycerin, crown ethers, aza crowns, cryptands, cyclophanes, oligo- and poly-peptides, proteins, oligo- and poly-nucleotides, or other similarly structured molecules, dispersed in an acid or other solvent medium.

In a second embodiment, the invention is a colloidal dispersion of nano-structured particles formed through the addition of selected guest solids to the novel structured fluid matrix.

In a third embodiment, the invention is a process for converting native or modified polysaccharides, cavitands, simple sugars, such as dextrose, fructose or glucose, simple (linear, branched, or cyclic) polyols, such as ethylene glycol, propylene glycol, or glycerin, crown ethers, aza crowns, cryptands, cyclophanes, oligo- and poly-peptides, proteins, oligo- and poly-nucleotides, and other similarly structured molecules into a structured fluid matrix and preparing nano-structured particles by adding selected guest solids to the structured fluid matrix to yield colloidal dispersions thereof.

In a further embodiment, the invention is a process for creating a stable nanoparticle colloidal dispersion by fusing small, supra-molecular host molecules into a clathrate cage encompassing the entire nanoparticle, e.g., by caramelizing cyclodextrins or other carbohydrates at the surface of the nanoparticle.

In another embodiment, the invention is a process for attaching useful moieties to a nanoparticle through the clathrate cage, e.g. through acetal or hydrazone linkages. This may include moieties that stabilize colloidal dispersions, for example by attaching charged groups that increase the zeta potential of the nanoparticles.

In yet a further embodiment, the invention is a distinctive process technology useful to prepare dispersions for jetting and other stable colloidal dispersions of nanoparticles, by initiating cavitation to reduce the size of solid guest particles in a high viscosity structured fluid.

The structured fluids of the invention are prepared by mixing components that are easily removed by membrane filtration. These components include, but are not limited to cavitands, modified polysaccharides, native polysaccharides, simple sugars, such as dextrose, fructose or glucose, simple polyols, such as ethylene glycol, propylene, glycerin, sorbitol, xylitol and the like, polyphosphoric acids, mixtures of two or more of these components, and combinations of the mixture with aldehydes or polyaldehydes.

DETAILED DESCRIPTION OF THE INVENTION

Figure 1:
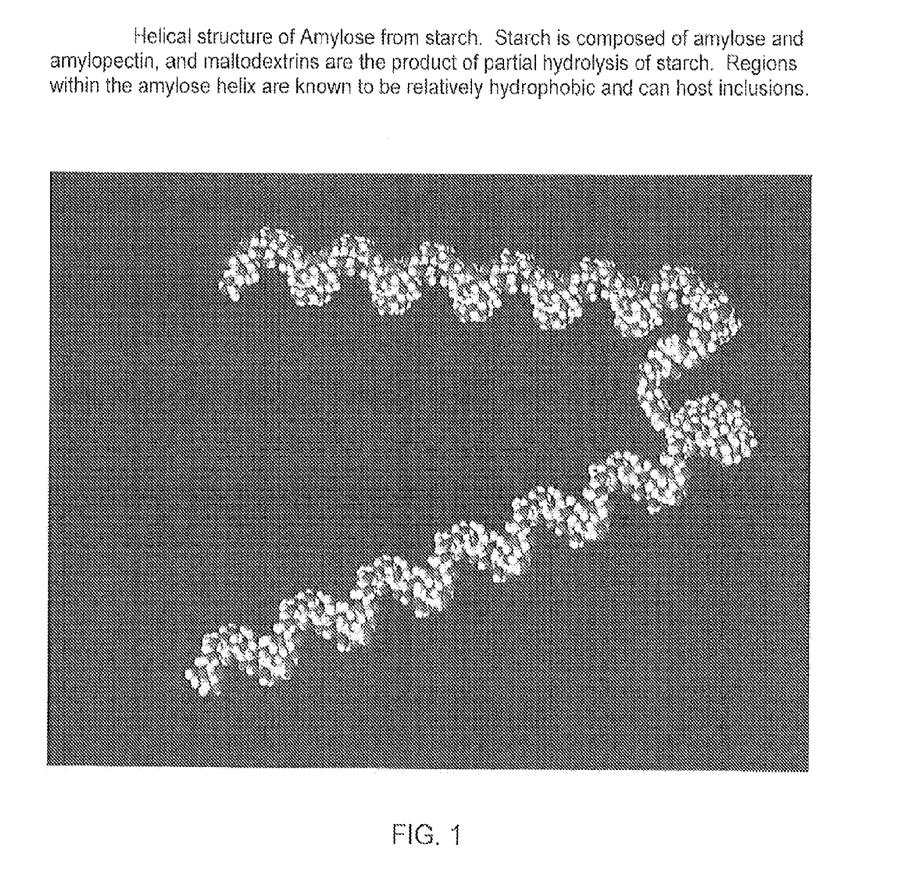
FIG. 1 shows the helical structure of amylose from starch.
Figure 2:
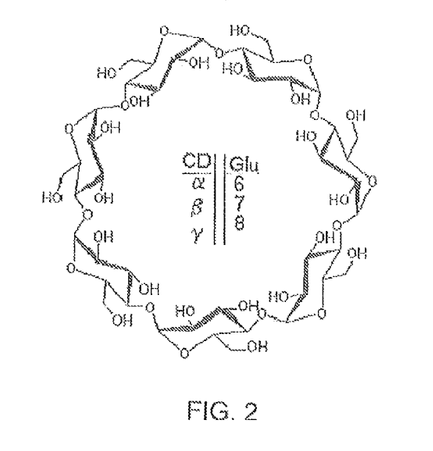
FIG. 2 is a chemical structure of β-cyclodextrin.
Figure 2A:
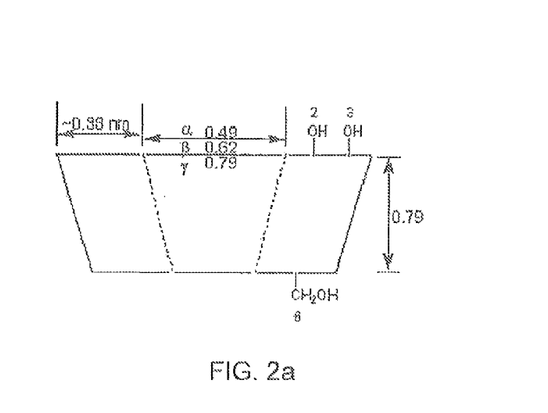
FIG. 2a is a schematic representing structures and dimensions for α, β, and γ-cyclodextrins.
Figure 3:
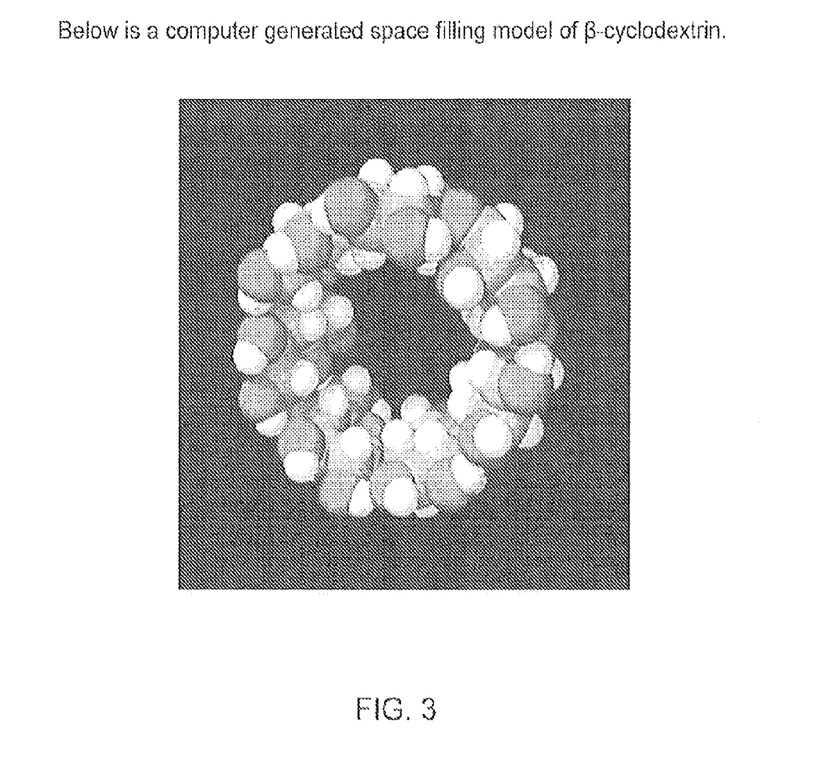
FIG. 3 shows a computer generated space filled model of β-cyclodextrin.

Before describing the inventive compositions and processes in detail, it should be understood that the invention is not limited to the specific components, amounts of components, or applications for use set forth herein. The inventions may include other embodiments and may be practiced in various ways, as one skilled in the art would understand from the description.

Terminology used herein is not intended to be limiting. The use of "including", "containing", "constituting", "comprising" or "having" and any other variations thereof is not limited to the items recited or listed and is intended to encompass equivalents and additional items. Use of singular terms are intended to include the plural form.

Numerical ranges described herein include all values from the lowest value to the highest value.

For the purposes of the present invention, the following terms are defined:

In our usage, a "nano-structured particle" or a "nanoparticle" is a particle that possesses structural features having dimensions on the scale of nanometers (such as, for example, the thickness of the clathrate cage).

Strictly speaking, a nanoparticle is generally considered to be a particle in which all dimensions are less than 100 nanometers, however such particles are often prepared as a distribution of sizes encompassing a range from particles smaller than 100 nm to particles that may be substantially larger. Distributions of particle sizes in which nearly all of the particles are less than 600 nm diameter, and the average particle size is less than about 200 nm diameter are most suitable for jetting. Average particle sizes of less than about 150 nm are particularly useful for jetting applications.

"Gel" means a colloid or solution in which a dispersed phase (solid) combines with a dispersion media (fluid) to form a semi-solid or viscoelastic material.

We use the term "gel" interchangeably with the terms "structured fluid", "structured fluid matrix", or "structured fluid host". With respect to the invention in particular, all of these terms mean and include the semi-solid or semi-rigid gel resulting from the mixing of host vessels (molecules), such as native or modified polysaccharides, cavitands, simple sugars, such as dextrose, fructose and glucose, simple (linear, branched, or cyclic) polyols, such as ethylene glycol, propylene glycol, glycerin, sorbitol, xylitol and the like, crown ethers, aza crowns, cryptands, cyclophanes, oligo- and poly-peptides, proteins, oligo- and poly-nucleotides, or other similar molecules in an acidic dispersing fluid. The use of the term "structure" is simply a reference to the control of the dimensions of void regions (regions without dissolved solid in which particle growth will be constrained), or it may be a higher order structure with liquid crystalline properties characterized by organization of the position and orientations of the dissolved solid.

"Template" refers to the functions/applications of the structured fluid as a form for reducing particle size or constraining the growth of the particle.

"Scaffold" means the support structure that is created by the clathrate cage, limiting agglomeration of the nanoparticles, thereby stabilizing the colloidal dispersion. The clathrate cage also provides points for attachment of other components to the added "guest" solid.

"Clathrate" means a composition in which the molecules of one substance (guest molecules) are physically trapped within the structure of another (host vessel). For purposes of this invention, clathrate also refers to the novel nanoparticle-based colloidal particles created by the addition of a guest solid to the structured fluid host.

The terms "host", "host vessel" and "clathrate cage or shell" are used interchangeably to describe the exterior portion of the clathrate that is trapping the solid in the interior.

"Stability" refers to the stability of the interaction between the components of the clathrate (i.e., the trapped particle and the "host vessel"), but it is also used to describe the colloidal stability of the dispersion (i.e., the tendency of the particles to remain dispersed and to not agglomerate). An effort is made to keep this distinction clear within the context of the discussion.

Other definitions are set forth throughout the description.

The novel nano-structured particles and colloidal dispersions of the present invention are based upon modifications of polysaccharides, cavitands, simple sugars, simple polyols, and other similarly structured molecules, all described herein, which are known to one skilled in the art to be useful host vessels.

Some classes of compounds possess organizational features within their structure known to promote the formation of strong, non-covalent bonding. These features allow them to play "host" very effectively for particular guest molecules. Prominent among these compounds are certain polysaccharides that adopt specific conformations including hydrophobic regions, defined hydrogen bonding and electrostatic orientations.

Compounds useful in the invention to prepare the structured fluid matrix and reduce the particle size of selected guest solids include but are not limited to certain native polysaccharides, such as amylose, and modified polysaccharides, such as maltodextrin and chitosan, and other similarly structured molecules, as well as related compounds, such as cyclodextrins, calixarene, and cucurbituril. Simple sugars, such as dextrose, fructose and glucose, and simple (linear, branched, or cyclic) polyols, such as ethylene glycol, propylene glycol, or glycerin, sorbitol, xylitol and the like, crown ethers, aza crowns, cryptands, cyclophanes, oligo- and poly-peptides, proteins, oligo- and poly-nucleotides, having or that are able to be modified to achieve specific conformations are also thought to be useful for the present invention.

Cyclodextrins, in particular, exhibit these organizational features to a greater degree due to the conformational constraints imposed by their cyclic structure. Cyclodextrins are members of a class of cyclic compounds known as cavitands that include, in addition to cyclodextrin, synthetic molecules with similar properties, such as calixarenes and cucurbiturils. Calixarenes and cucurbiturils and other cavitands are considered to be within the scope of the invention. Other similarly structured compounds having similar organizational features useful in the present invention are known to one skilled in the art It has been discovered that when the "host" compounds are dissolved or dispersed within certain acidic fluids or other solvents, they form a viscoelastic or semi-solid gel, which is a "structured" fluid matrix having regions within the fluid that act as a template to reduce the particle size of an introduced solid to nanoparticle dimensions or to control the growth of small particles. During and after the formation of these small particles, a clathrate cage forms around the nanoparticle. The structure of this cage is derived from a portion of the gel template. Any excess of the gel template remains free and may be easily purified or otherwise removed from the clathrate dispersion after the reaction.

The novel nanoparticles of the present invention are prepared by controlling formation of the particles, and thus their size, upon addition of a selected guest solid to a "structured" fluid matrix comprising a gel prepared from a host vessel comprising certain native or modified polysaccharides, cavitands, simple sugars, such as dextrose, fructose and glucose, and simple (linear, branched, or cyclic) polyols, such as ethylene glycol, propylene glycol, or glycerin, sorbitol, xylitol and the like, crown ethers, aza crowns, cryptands, cyclophanes, oligo- and poly-peptides, proteins, oligo- and poly-nucleotides, or other similarly structured molecules known to be useful host molecules in supramolecular chemistry, dispersed in a fluid such as a polyphosphoric acid, particularly superphosphoric acid (105%), sulfuric acid (~80 wt. % aq.) or glyoxylic acid (50% aq.). For superphosphoric acid, the percentage greater than 100% indicates the ability to absorb water by hydrolyzing phosphoric anhydride bonds. Other concentrations of these components and other acids and solvents can also be used, provided that they facilitate the formation of the structured fluid matrix.

It is believed that the particle size reduction of the selected guest solid proceeds via larger particles dissolving and then recrystallizing within the template created by the structured fluid. Particle size reduction may be driven in part by increasing the surface area of the selected solid particles within the structured fluid matrix to create more interfaces with the surfaces of the host vessel. Ultimately, the scaffold reduces the particle size of the selected solid upon recrystallization and limits the particle size achieved to nano-structured particles. The nanoparticles are thus captured within the clathrate, wherein the nanoparticles are encompassed by a clathrate cage formed from the fusion of molecules of the host vessel at the surface of the nanoparticles.

Following processing, the nanoparticles thus prepared retain a portion of the structured fluid matrix as a vessel or "host" structure for the added "guest", i.e., selected solid. This host/guest combination is a clathrate cage with a nanoparticle attached to or located within the structure, resulting from trapping the guest particle within, or attachment of the guest particle to, the host vessel. The composition of the clathrate cage is derived from a portion of the particular solid that is dissolved, as the guest, in the structured fluid matrix. Following the quench of the reaction with water and the adjustment of pH, removal of salts and the other components of the gel not attached to the nanoparticles yields a stable colloidal dispersion.

In the dispersion, the clathrate is believed to stabilize the dispersion, inhibit agglomeration between guest particles and serve as a scaffold for attachment of other molecules to the surface of the guest particle. These attachments may include charged functional groups that increase zeta-potential, further inhibit agglomeration and enhance the stability of colloidal dispersions prepared from the particles. Additional stabilization steps are not required by the inventive process.

Other mechanisms may also contribute to the stability of the colloidal dispersions described herein. In particular, for certain host vessels, discussed below, caramelization may be involved in the stabilization of the resulting nanoparticle colloidal dispersion. Caramelization may be promoted by the acidity and dehydrating conditions resulting from the use of superphosphoric acid and more concentrated sulfuric acid. Acids also have the ability to dissolve solids like pigments, for example, that have very strong intra-molecular attractions between the molecules of the solid, and which are not very soluble in most other solvents. This may be because the acidity tends to weaken certain intra-molecular attractions, such as hydrogen bonds. For this reason, acids may be preferred solvents, although the invention is not so limited.

Extreme caramelization should be avoided because it may result in larger particles and a less stable colloid. Hence, depending on the host vessel used to form the gel, the concentrations of the acids or other solvents may vary. For example, with maltodextrin, if the concentration of sulfuric or other acid is too high, "charring" carbonization will occur, which is a very extreme example of caramelization.

Carbohydrates, in particular, including without limitation polysaccharides and cyclodextrins, undergo caramelization reactions. These reactions typically proceed at temperatures in excess of 100° C.; however, it is known that they are promoted under acidic and dehydrating conditions that are found, for example, in the reactions in polyphosphoric (superphosphoric 105%) acid, sulfuric acid (80 wt. % aq.), or glyoxylic acid (50% aq.) described herein. It is believed that caramelization may strengthen or contribute to the strength and stability of the resultant clathrate cage structure and may help to increase the colloidal stability of the particle dispersion, by increasing the hydrophilic characteristics of the host vessel surrounding the guest particles. It is also possible that caramelization may introduce new chemical moieties, such as ketones that can serve as "handles" for attachment of other groups to the particle, or it may directly result in the formation of acidic groups on the surface of the vessel surrounding the guest particle that increases the zeta potential and thus stabilizes the colloid. Use of aldehydes, such as glyoxylic acid, may also contribute to and facilitate attachments or linkages between host vessel molecules and guest solids.

While not wishing to be bound by any particular theory, it is believed that the selected host vessel, when dispersed in liquid acid medium (or other solvent), forms regions within the resulting structured fluid matrix wherein particle growth is constrained. The guest material added to the structured fluid may become organized within these regions, both while being dissolved and also while recrystallization occurs such that the particle size is reduced and the $-\Delta G$ (Free Energy change) for the interaction between the guest material and the host region is maximized in an annealing process. This Free Energy change for the interaction between the guest material and the host region connotes non-covalent bonding interactions and attractive forces between them, including non-polar (hydrophobic and Van der Waals), $\pi$-stacking, polar, and hydrogen bonding. The $-\Delta G$ (negative change in free energy denoting a process that will be spontaneous) for this interaction may help to drive the particle size reduction of the guest material so that the contact area between the surfaces of the guest material and the host region is increased. Following a quenching step, the interactions between the host region and guest material are substantially locked into place.

From another view of the inventive process, the attractive forces between the surface of the guest particle and the structured fluid may be described as adhesive forces between the particle and the fluid. Solutions and dispersions of polysaccharides, and other carbohydrates, including cyclodextrins and even simple sugars and polyols, are widely understood to be "sticky". In addition, the time required for rearrangements of structure within these fluids can lead to viscoelastic behavior wherein the viscosity of the fluid varies depending upon the time scale of the force applied to the fluid. Breaking the adhesion between a particle surface and a viscoelastic or sticky fluid matrix can require more than 10,000 times the amount of energy released in the formation of the adhesive interaction. The reasons for this remain obscure.

Among other contributions, the energy change has been attributed to the separation of molecular entanglements formed between the adhered surfaces, interfacial instabilities, and even cavitation (Zhao, Zeng, Tian, and Israelichvili; *PNAS,* 2006: Vol. 103, No. 52, 19624-19629). Cavitation is a source of highly focal energy that is very useful for particle size reduction. Recent published work predicted that higher viscosity promotes the inception of cavitation at lower flow velocity (Padrino, Joseph, Funada, Wang, Sirigano; *J. Fluid Mech.,* 2007: Vol. 578, pp. 381-411). This work also cited experimental evidence to support the onset of cavitation at lower flow rates in more viscous fluids.

Prior art technologies to prepare stable colloids of nanoparticles, particularly for jetting, promote cavitation either through fluid flow impingement or in ultrasonic fields. Notably, for many applications in which a colloidal dispersion of small particles is required, high viscosity is undesirable. This is particularly true for colloidal dispersions prepared for jetting applications. It is a feature of the inventive processes that the structured fluid matrix has high viscosity during particle size reduction. In addition, host components of the structured fluid matrix that are not utilized in the formation of the clathrate surrounding the guest particle are easily removed following the quench of the reaction, for example, by membrane ultra-filtration, thus reducing the viscosity. This facilitates the process of reducing particle size easily and efficiently in a high viscosity structured fluid matrix to prepare stable colloids of small particles, while remaining at a suitable viscosity for jetting applications.

Hence, the inventive process is distinct from prior art processes wherein particle size is reduced in a high viscosity medium and the viscosity remains high in the final colloidal dispersion of particles. The inventive process unexpectedly yields rapid reduction of particle size even at low fluid velocity and is a unique, distinctive technology to reduce particle size by initiating cavitation in a high viscosity structured fluid that is easily rendered into a low viscosity colloidal dispersion of small particles by simple processing, such as membrane ultra-filtration. The inventive stable colloidal dispersions are useful for the preparation of dispersions for jetting and other stable colloidal dispersions of particles.

Much of the energy that is applied to separate adhered surfaces dissipates in the deformation of the bulk material (Ruths and Granick, Langmuir Vol. 14, No. 7, 1804-1814). This deformation can contribute to the breakdown of the cohesive forces that hold the particle together. Reduction of the size of particles entrained within the structured fluid can occur as these attractive forces overcome the cohesive forces within the particle.

It is further known that nano-structures, such as graphene, can be formed by peeling layers off of the surface of a material that is adhered to the surface of another material, such as an adhesive tape. Likewise, the structured fluid may efficiently couple the mixing energy to pull the guest particle apart, which is distinct from typical methods of particle size reduction that break the particle down by impact from media or a shock wave. Even relatively slow rates of the flow of the structured fluid may pull the guest particle apart, possibly by focusing the mixing energy to move sequentially along the length of a crystalline phase of the selected guest solid and "unzip" the interactions between the facets of the crystal, thus reducing the particle size. Further, at these slower rates of flow, the host components of the structured fluid have increased time to reorganize at the newly formed particle surface, and to maximize the attractive forces between the host components of the fluid and the guest particle.

Accordingly, the inventive process is a distinctive technology that focuses mechanical energy to reduce particle size to form a colloid within a condensed phase (the gel) for the preparation of dispersions for jetting and other stable colloidal dispersions of particles, which differs significantly from heretofore described abrasive or shock wave impact processes for particle size reduction. In addition, the chemical properties of the structured fluid matrix, such as for example the pH, may serve to decrease the cohesive properties within the guest particles even when the particles are not dissolved. This may be done, e.g., by weakening hydrogen bonding within the particle, by protonating hydrogen bond acceptors, or by deprotonating hydrogen bond donors making them more susceptible to particle size reduction by this "peeling" process.

In summary, the inventive processes achieve excellent and surprising particle size reduction, without media milling, ultra-sonics, or high velocity fluid flow. They also achieve unexpected high colloidal stability of the resultant nanoparticles, without adding surfactants or polymers or covalently attaching reactive intermediates to the particle surface. While not wishing to be bound by any particular theory, it is believed that unlike the prior art techniques for preparing stable colloids of nanoparticles, particularly for jetting, the inventive processes:

1. Reduce the size of particles by dissolving and recrystallizing them in a structured fluid matrix that constrains their growth and promotes particle size reduction by increased attraction ($-\Delta G$) between the increased surface area of the particles and the host components of the structured fluid.

2. Reduce the size of particles by promoting cavitation, induced by mixing (mechanical) energy in a high viscosity structured fluid even at low fluid velocities.

3. Reduce the size of particles by efficiently coupling mixing (mechanical) energy through attractive interactions between the structured fluid and the particle surface to peel layers from the surface of the particle even at low fluid velocities.

4. Stabilize the increased surface area of the nanoparticles by fusing components of the structured fluid matrix through caramelization, or transglycosylation between sugars, or cross-linking through an acetal to form a clathrate with the particle.

5. Stabilize the colloidal dispersion of the nanoparticles by increasing the zeta potential through charged groups at the surface of the clathrate derived from acidic groups formed by caramelization, charged groups attached to the clathrate through acetals, or charged groups attached to the clathrate through other chemistries.

It is a critical feature of the invention that the components forming the structured fluid matrix (i.e. host vessels), which are not strongly bound (non-covalently) to the guest particle, may be separated, such that the final product is a dispersion of nano-structured particles containing a core of guest particles surrounded by a host vessel (the clathrate cage) formed within the structured fluid matrix. This separation is necessary so that the final product may be obtained with the desired concentration of guest material and in the desired particle size range, and with the desired viscosity, all of which are essential when the particles are being prepared for jetting applications.

Separation may be accomplished, preferably, by a membrane ultra-filtration process. It is therefore a feature of this invention that the host vessel components and liquid used to form the structured fluid are able to pass across the ultra-filtration membrane while the clathrate product, i.e., host/guest particles, is retained. The invention provides a structured fluid matrix using selected host vessel components, as described above, many of which are at, or smaller than, the scale of the desired final particles. This is accomplished by selecting host components having the desired scale. However, the invention does not require host components of any particular scale. For this reason, if larger polysaccharides, cavitands or other host vessels in liquid are used to form the structured fluid, their use requires a digestion or other pre-processing step to reduce them to components that will easily pass across the ultra-filtration membrane. This digestion may involve, for example, hydrolysis or other cleavage by oxidative or free radical digestion steps. Care must be taken so that the digestion steps do not interfere with the formation of the nanoparticles and/or degrade or damage the desired properties of the final particles.

For example, starch may be pre-digested to smaller scale components before addition of the guest material, or only the smaller amylose component and not the amylopectin component of starch may be utilized. Alternatively, one can begin with an already modified form of a polysaccharide, such as, for example, maltodextrin. As another alternative, and surprisingly, it has been discovered that much smaller molecules, such as the cavitands (e.g., cyclodextrins, calixarenes, and cucurbiturils), may be used as host vessels to form the structured fluid matrix. Excess maltodextrins or cavitands may then be easily removed by the membrane ultra-filtration described above, or by other methods known to those skilled in the art.

Host components useful in the invention have been described above. Other similarly structured molecules known to one skilled in the art to be useful host vessels in supramolecular chemistry applications are also within the scope of the invention.

A wide variety of selected guest solids may be used in the inventive process. Particularly useful pigments for inclusion as guest particles include without limitation: Pigment Red 122, solid solutions of mixed quinacridones such as Cinquasia® Magenta D 4500 J (solid solution of quinacridones), Pigment Blue 15, Pigment Green 7, Pigment Green 36, Pigment Yellow 74, Pigment Yellow 180, Pigment Yellow 120, or Pigment Red 177, or carbon black or graphite. Other classes of colored pigments include, for example, anthraquinones, phthalocyanine blues, phthalocyanine greens, diazos, monoazos, pyranthrones, perylenes, heterocyclic yellows, quinacridones, and (thio) indigoids. Representative examples of quinacridones include Pigment Orange 48, Pigment Orange 49, Pigment Red 122, Pigment Red 192, Pigment Red 202, Pigment Red 206, Pigment Red 207, Pigment Red 209, Pigment Violet 19 and Pigment Violet 42. Representative examples of anthraquinones include Pigment Red 43, Pigment Red 104 (Perinone Red), Pigment Red 216 (Brominated Pyranthrone Red) and Pigment Red 226 (Pyranthrone Red). Representative examples of perylenes include Pigment Red 128, Pigment Red 149, Pigment Red 168 (dibromoanthanthrone available from Clariant as SCARLET GO), Pigment Red 179, Pigment Red 190, Pigment Violet 19, Pigment Red 189, and Pigment Red 224. Representative examples of thioindigoids include Pigment Red 86, Pigment Red 87, Pigment Red 88, Pigment Red 181, Pigment Red 198, Pigment Violet 36, and Pigment Violet 38. Representative examples of heterocyclic yellows include Pigment yellow 1, Pigment yellow 3, Pigment Yellow 12, Pigment Yellow 13, Pigment Yellow 14, Pigment Yellow 17, Pigment Yellow 65, Pigment Yellow 73, Pigment Yellow 74, Pigment Yellow 151, Pigment Yellow 117, Pigment Yellow 128, Pigment Yellow 138, and Yellow Pigment 155. Other pigments useful in the present invention will be obvious to one skilled in the art.

Other suitable solids for inclusion as guest particles include colorants, dyes, scents, flavors, fragrances, chemicals, both organic and mineral, metals and metal ions, pharmaceuticals, chemical indicators, biological indicators, biological molecules, biological sensors and analytes, reagents, and the like.

While particle size reduction by milling may be used in conjunction with the present methods, depending on the guest solid selected, it is typically not required to obtain particle size reduction, except when the dimensions of the molecular components of the guest solid selected for inclusion are much larger than the desired particle size or agglomerated via covalent bonds, as in the case of some carbon blacks. In any event, the particle size reduction occurring prior to introducing the selected solid to the structured fluid matrix is not intended to result in nanoparticles, but rather to facilitate the formation of nanoparticles in the inventive process.

The method of preparing the inventive compositions is done in one mixing step, with all components being added in sequence. An acidic fluid or other solvent medium with agitation while adding a modified polysaccharide, cavitand or other similarly structured molecule, followed by the addition of the selected solid, also with agitation. This mixture is continually heated and stirred at a set temperature and for a set period of time to achieve particle size reduction and annealing. Quenching and subsequent filtration yield a pure stabilized product that is a stable nanoparticle-based colloid dispersion. No separate particle size reduction or colloidal stabilization steps are necessary.

In some instances, upon completion of the size reduction/annealing stage, additional components may be added to the reaction, such as sulfuric acid, and the mixture will continue to be heated at a set temperature and stirred for an additional time period. This additional step may be useful when the primary solvent used to form the structured fluid matrix (gel) is glyoxylic acid. Glyoxylic acid contains a carboxylic acid directly attached to an aldehyde group. The aldehyde group can be attached to hydroxyl groups on the cyclodextrins or polysaccharides through an acetal linkage, and the formation of the acetal linkage is usually promoted with the addition of some mineral acid, such as sulfuric acid. The rationale for reacting cyclodextrin with glyoxylic acid and later sulfuric acid is that it may promote connections between the cyclodextrins or polysaccharides and thus strengthen the clathrate cage and, further, may promote caramelization of the polysaccharide. Other similar modifications of the process may be included; however, the key is that the nanoparticle-based colloidal dispersion is still created by combining all components in one step, with additional process modifications useful to stabilize the dispersion further.

Temperatures employed in the process generally range from about 40° C. to 100° C. during component mixing phase and from about 40° C. to 100° C. during the size reduction/annealing phase, although slightly lower or higher temperatures may be used.

Quenching is usually accomplished with the addition of water; however, other components may be used for quenching. The addition of water reduces the solubility of the pigment (or other selected solid) in the dispersion, so that the particle size is no longer changing. It may also slow down or stop reactions involving the cyclodextrins or other polysaccharides, such as caramelization.

The quenching solution may include other components to aid stabilization, such as glyoxylic acid, or other compounds that may react to attach covalently to the clathrate cage. The idea behind the use of glyoxylic acid in quenching is to facilitate attachment between hydroxyl groups of cyclodextrins, polysaccharides, sugars, or calixarenes through acetal linkages strengthening the clathrate, and also to increase the zeta potential on the particle by attachment of a charged carboxylate group to the surface of the particle further stabilizing the dispersion.

Other useful quenching compounds that facilitate attachments and further stabilize the dispersion include other aldehydes, which can react to form hemi-acetals and acetals, hydrazines, hydroxylamines, amines, epoxides, acceptors for nucleophilic conjugate additions, such as acrylic acid or acrylate esters, conjugated dienes, dieneophiles and other compounds that can react with nucleophiles (such as hydroxyl groups), electrophiles (such as carbonyl groups), conjugated dienes (such as furans), or dieneophiles in the clathrate cage. These compounds may also be attached to the clathrate cage at a later stage than the quench of the reaction, for example after the pH has been adjusted and also after the particles have been purified, for example by filtration, centrifugation or ultra-filtration. Compounds that are attached to the clathrate may be used to modify the properties of the clathrate. For example, compounds bearing charged groups may be attached to the clathrate to increase the zeta potential of the particle and to help improve the colloidal stability of a dispersion of the particles. Alternatively, groups may be attached that can increase the affinity of the particles for particular substrates such as paper or textiles, or to modulate affinity even more specifically, for example by biotinylation or even by attachment of antibodies.

Base compounds may be added to neutralize the acid. Suitable acid neutralizing compounds include sodium, potassium, or other alkali metal carbonates, sodium, potassium, or other alkali metal bicarbonates, sodium, potassium or other alkali metal hydroxides, ammonia or ammonium compounds, and organic amines. Other neutralizing compounds would be well known to one skilled in the art.

The invention is illustrated through several embodiments generally described below and in the examples.

In one preferred embodiment, the gel is prepared by heating a polyphosphoric acid (superphosphoric acid 105%), with agitation, while adding maltodextrin (MALTRIN M100) with agitation. The clathrate is then formed by adding the selected guest particles to the gel, also with agitation. An alternative embodiment for forming the gel may include using even smaller carbohydrate oligomers, corn syrup, and the like or even simple sugars, such as dextrose, fructose or glucose, or polyols such as ethylene glycol, glycerin, sorbitol, xylitol and the like.

In another preferred embodiment, the gel is prepared by heating a polyphosphoric acid (superphosphoric acid 105%), with agitation, while adding β-cyclodextrin (CAVAMAX W7) with agitation. The clathrate is then formed by adding the selected guest particles, also with agitation.

In yet another preferred embodiment, the gel is prepared by heating glyoxylic acid (50%), with agitation, while adding β-cyclodextrin (CAVAMAX W7) with agitation. An alternative embodiment for forming the gel may include using even smaller carbohydrate oligomers, corn syrup, and the like or even simple sugars or polyols such as ethylene glycol, glycerin, sorbitol, etc. The clathrate is then formed by adding the selected guest particles, also with agitation.

The novel nanoparticle-based clathrates described herein may be used in various applications. Although the primary application described herein is for colloidal pigment dispersions, other valuable applications include, for example:

a. therapeutic novel pharmaceutical compositions, nanotechnology based drug delivery systems, medical diagnostics and biotechnology;
b. delivery and preservation of high value compounds, such as natural colorants, flavors, fragrances, and the like;
c. micro-fluidics;
d. chemical sensors or indicators;
e. chemical extraction and chemical manufacturing processes;
f. materials science, materials jetting and materials manufacturing; and
g. electronics and electronic materials jetting and manufacture.

Other applications will be apparent to those skilled in the art.

EXAMPLES

Example 1

Preparation of a Self-Assembled Nanoparticle Based Colloidal Pigment Dispersion Using Maltodextrin In this example, polyphosphoric acid (superphosphoric acid 105%) was heated, with agitation, and maltodextrin (MALTRIN M-100) was added with agitation. The final mass ratio was approximately 1.06 maltodextrin to 1.00 superphosphoric acid (105%).

At a temperature between about 80° C. and 100° C., color pigment chosen from Pigment Red 122, Pigment Blue 15, or Pigment Yellow 74 was added to the gel with agitation. The final mass ratio was approximately 0.2 pigment to 1.00 superphosphoric acid 105%. Following this, the gel was stirred at elevated temperature for size reduction and annealing for some period of time. Upon completion of the size reduction/annealing period, the reaction was quenched by the addition of water to the reaction mixture.

Example 2

Preparation of a Self-Assembled Nanoparticle-Based Colloidal Pigment Dispersion Using Cyclodextrin In this example, polyphosphoric acid was heated, with agitation, and β-cyclodextrin (CAVAMAX W7) was added with agitation.

The final mass ratio was approximately 1.06 β-cyclodextrin to 1.00 superphosphoric acid 105%. At a temperature between about 40° C. and 60° C., color pigment chosen from Pigment Red 122, Pigment Blue 15, Pigment Green 7, Pigment Green 36, or Pigment Yellow 74 was added to the gel with agitation. The final mass ratio was approximately 0.2 pigment to 1.00 superphosphoric acid 105%. Following this, the gel/pigment mixture was stirred at elevated temperature for size reduction and annealing for some period of time. Upon completion of the size reduction/annealing period, the reaction was quenched by the addition of water to the reaction mixture or by the addition of the reaction mixture to water.

Example 3

Preparation of a Self-Assembled Nanoparticle-Based Colloidal Dispersion of Pigment Using Cyclodextrin In this example, glyoxylic acid (50%) was heated, with agitation, while adding β-cyclodextrin (CAVAMAX W7) with agitation.

The final mass ratio was approximately 1.99 β-cyclodextrin to 1.00 glyoxylic acid (50%) aqueous. At a temperature of between about 40° to about 60° C., Pigment Yellow 180 was added to the gel fluid with agitation. In this specific example, the final mass ratio was approximately 0.083 pigment to 1.00 glyoxylic acid (50%) aqueous. Following this, the gel/pigment mixture was stirred at elevated temperature for size reduction and annealing for some period of time. Upon completion of the size reduction/annealing period, 0.9 parts (relative to 1.00 part of glyoxylic acid (50%) aqueous) of concentrated sulfuric acid (about 93-98%) was added to the reaction, stirred, and heated at 60° C. for an additional 6 hours prior to quenching by the addition of water.

Example 4

Particle Size Reduction by Milling of Carbon Black

The process of example 3 was modified to include particle size reduction by milling in the case of carbon black as the selected solid/pigment.

Example 5

Preparation of a Self-Assembled Nanoparticle-Based Colloidal Pigment Dispersion Using Cyclodextrin The Process of example 2 was modified to include a final mass ratio of approximately 0.4 color pigment chosen from Pigment Red 122, Cinquasia® Magenta D 4500 J, Pigment Blue 15, or Pigment Yellow 180 to 1.00 superphosphoric acid 105% to approximately 1.06 β-cyclodextrin. Following this, the gel/pigment mixture was stirred at elevated temperature for size reduction and annealing for some period of time. Upon completion of the size reduction/annealing period, the reaction was quenched by the addition of the reaction mixture to water.

Example 6

Preparation of a Self-Assembled Nanoparticle-Based Colloidal Pigment Dispersion Using Cyclodextrin The Process of example 3 was modified to include a final mass ratio of approximately 1.99 β-cyclodextrin to 1.00 glyoxylic acid (50%) aqueous to 0.25 color pigment chosen from Pigment Yellow 180, Pigment Yellow 120, or Pigment Red 177 to 1.00 glyoxylic acid (50%) aqueous. Following this, the gel/pigment mixture was stirred at elevated temperature for size reduction and annealing for some period of time. Upon completion of the size reduction/annealing period, 1.35 parts (relative to 1.00 part of glyoxylic acid (50%) aqueous) of concentrated sulfuric acid (about 93-98%) was added to the reaction, stirred, and heated at 60° C. for an additional 4 hours prior to quenching by the addition of the reaction mixture to water.

Example 7

Preparation of a Self-Assembled Nanoparticle-Based Colloidal Pigment Dispersion Using Cyclodextrin The Process of example 3 was extended to include addition of approximately 0.5 parts glacial acetic acid (relative to 1.00 part of glyoxylic acid (50%) aqueous) to the reaction mixture.

In the above examples, quenching was performed by the addition of water or by the addition of the reaction mixture to water. The quenching solution may also comprise another component, such as glyoxylic acid or other aldehyde such as formaldehyde or glutaraldehyde or other polyaldehyde, to improve the stability of the final product, for the reasons discussed above. Other acids may be added to the quenching solution as well. The quenching water may also contain a base to help neutralize the acidic mixture, such as sodium carbonate or sodium hydroxide.

The reaction mixtures resulting from the addition of the pigments to the gel may, after the size reduction/annealing period, continue to be mixed at a set temperature for a set duration until they are mixed into a larger volume of water.

After the final quench of the reaction mixtures, membrane ultra-filtration was performed to remove components of the structured fluid matrix that were not incorporated into the nanoparticles and other impurities, while retaining the nanoparticles. The purification step helped to stabilize the dispersions.

Following the membrane ultra-filtration step, larger and less stable particles were removed from the dispersion, by settling and decantation, centrifugation, filtration or by some combination of these. The dispersions thus prepared showed excellent colloidal stability.

Inks prepared using the above colloidal dispersions of organic color pigments demonstrated excellent jetting properties, which were demonstrated using an HP B 8850 A3 thermal pigment printer.

Example 8

Analysis of Composition

Data (see Tables 1-3 below) obtained by the use of self-dispersed copper phthalocyanine prepared according to example 2 in a gel of 3-cyclodextrin in superphosphoric acid (105%) indicated that very little phosphate or polyphosphate remained attached to the nano-structured particles formed using the gel. The spectroscopic data indicated that the surface of the particles was characterized by a high content of highly oxygenated carbon, including ketones and carboxylic acid. Hence, it is believed and the data supports that the reaction promoted a caramelization between the cyclodextrin molecules forming the clathrate cage around the particle. Carboxylic acids formed by the process may also be a critical factor contributing to the stability of colloidal dispersions of these particles. Data from TOF-SIM have been interpreted to show the absence of un-modified β-cyclodextrin. This finding helped to distinguish the inventive process from the prior art.

Bulk Particle Element Concentration [PPM wt]
  C~62 wt %
  N 14 wt %
  O 5.2 wt %
  S<10 PPM
  H 3.1 wt %
C, S determined by Combustion-IR
N, H determined by IGF-TC
O determined by IGF-NDIR

TABLE 1

Particle Surface Atomic Concentrations (in %) by XPS[a]

| Sample | C | N | O | Na | S | Cu | N/Cu |
|---|---|---|---|---|---|---|---|
| Self Dispersed Cu Phthalocyanine | 73.6 | 14.8 | 8.5 | 0.7 | 0.1 | 2.3 | 6.5 |
| Cu phthalocyanine powder | 74.8 | 19.9 | 2.3 | — | — | 3.0 | 6.6 |

[a]Normalized to 100% of the elements detected. XPS does not detect H or He.
[b]A dash line "—" indicates the element is not detected.

TABLE 2

Carbon Chemical States (in % of Total C) by XPS

| Sample | C—C, H | CN2 | C—O | C=O/O—C—O | C2NCu | O—C=O | Shake-up* |
|---|---|---|---|---|---|---|---|
| Self Dispersed Cu Phthalocyanine | 57 | 19 | 7 | 4 | 3 | 2 | 8 |
| Cu phthalocyanine powder | 67 | 23 | — | — | 4 | — | 7 |

*The Shake-up structure in a spectrum is resultant of a π→π* transition often indicative of aromaticity.

TABLE 3

Oxygen Chemical States (in % of Total O) by XPS

| | Sample | | |
|---|---|---|---|
| | C=O | C—O | H2O |
| Self Dispersed Cu Phthalocyanine | 12 | 77 | 11 |

Example 9

Analysis of Composition

Data (see Tables 4-6 below) obtained by the use of self-dispersed Pigment Yellow 180 prepared according to example 6 in a gel of β-cyclodextrin in glyoxylic acid (50% aqueous) indicated that the surface of the particles was characterized by a high content of highly oxygenated carbon, including ketones and carboxylic acid. Hence, it is believed and the data supports that the reaction promoted an acetal formation between glyoxylic acid and/or caramelization between the cyclodextrin molecules forming the clathrate cage around the particle. Carboxylic acids formed by the process may also be a critical factor contributing to the stability of colloidal dispersions of these particles. Data from TOF-SIM have been interpreted to show the absence of un-modified β-cyclodextrin. This finding helped to distinguish the inventive process from the prior art. TOF-SIM did detect a significant peak attributed to glyoxylic acid.

TABLE 4

Atomic Concentrations (in atomic %)[a]

| Sample | C | N | O | Na | Cl |
|---|---|---|---|---|---|
| Self-Dispersed Pigment Yellow 180 | 73.8 | 10.5 | 14.9 | 0.8 | 0.1 |

[a]Normalized to 100% of the elements detected. XPS does not detect H or He.

TABLE 5

Carbon Chemical States (in % of Total C)

| Sample | C—C/C—H | C—O/C—N | C=O/ O—C—N | O=C—O |
|---|---|---|---|---|
| Self-Dispersed Pigment Yellow 180 | 70 | 20 | 8 | 2 |

TABLE 6

Oxygen Chemical States (in % of Total O)

| Sample | C=O | C—O | H$_2$O? |
|---|---|---|---|
| Self-Dispersed Pigment Yellow 180 | 53 | 45 | 2 |

In accordance with the patent statutes, the best mode and preferred embodiments have been set forth, the scope of the invention is not limited thereto, but rather by the scope of the attached claims.

What is claimed is:

1. A process for forming a nanoparticle-based clathrate pigment composition, consisting of the steps of:
    preparing a high viscosity, structured fluid matrix by heating a concentrated acid medium consisting essentially of polyphosphoric (superphosphoric 105%) acid, sulfuric acid (80 wt. % aq.), or glyoxylic acid (50% aq.) or mixtures thereof, with agitation, and adding a host vessel molecule comprising a carbohydrate that is amylose, maltodextrin or cyclodextrin, with agitation, to the acid medium,
    adding a solid guest particle that is a pigment, with agitation, to the structured fluid matrix to form a mixture,
    stirring the mixture at an elevated temperature for a set period of time to allow for particle size reduction and annealing of the added solid quest particles as they become physically trapped within the host vessel molecule,
    quenching the mixture, and
    separating unreacted host vessel molecules from the mixture to obtain a stabilized lower viscosity colloidal dispersion of nanoparticle-based clathrates comprising the solid guest particle pigment within the host vessel molecules of the structured fluid matrix,
    wherein the particle size of the clathrate achieved by the process is less than about 600 nanometers.

2. The process of claim 1 wherein:
    the mixture is quenched by water.

3. The process of claim 1, wherein the temperatures under which the process is conducted range from 40 to 100° C.

4. The process of claim 2, wherein the quenching water further comprises a stabilizing compound comprising glyoxylic acid, sulfuric acid, aldehydes, hydrazines, hydroxylamines, amines, epoxides, acrylic acid, acrylate esters, conjugated dienes, dieneophiles or mixtures thereof, an acid neutralizing compound, or combinations thereof.

5. The process of claim 2, wherein the pigment comprises Pigment Red 122, Pigment Red 177, Magenta D 4500 J, Pigment Blue 15, Pigment Green 7, Pigment Green 36, Pigment Yellow 74, Pigment Yellow 120, Pigment Yellow 180, carbon black or graphite.

6. A colloidal dispersion of nanoparticle-based clathrates formed by the process of claim 1.

7. An ink jet composition comprising the colloidal dispersion of claim 6.

* * * * *

UNITED STATES PATENT AND TRADEMARK OFFICE
CERTIFICATE OF CORRECTION

| | | |
|---|---|---|
| PATENT NO. | : 9,458,322 B2 | Page 1 of 1 |
| APPLICATION NO. | : 14/346339 | |
| DATED | : October 4, 2016 | |
| INVENTOR(S) | : Duncan et al. | |

It is certified that error appears in the above-identified patent and that said Letters Patent is hereby corrected as shown below:

In the Specification

Column 17, Line 65, replace "in a gel of 3-cyclodexrin" with --in a gel of β-cyclodextrin--

In the Claims

Column 20, Line 17, Claim 1 replace "the added solid quest particles" with --the added solid guest particles--

Signed and Sealed this
Third Day of January, 2017

Michelle K. Lee
*Director of the United States Patent and Trademark Office*